United States Patent [19]

Gindler

[11] 4,125,377

[45] Nov. 14, 1978

[54] DETERMINATION OF TRIGLYCERIDES

[75] Inventor: E. Melvin Gindler, Rockford, Ill.

[73] Assignee: Pierce Chemical Company, Rockford, Ill.

[21] Appl. No.: 854,792

[22] Filed: Nov. 25, 1977

Related U.S. Application Data

[63] Continuation of Ser. No. 747,357, Dec. 3, 1976, abandoned.

[51] Int. Cl.² ............................................. G01N 33/16
[52] U.S. Cl. .................................................. 23/230 B
[58] Field of Search ......................... 23/230 B, 230 R

[56] References Cited

U.S. PATENT DOCUMENTS 4,012,287   3/1977   Carl et al. ....................... 23/230 BX

OTHER PUBLICATIONS

Henry; R. J., Clinical Chemistry Principles & Technics, Harper & Row, 1964, pp. 866-870.

Primary Examiner—Robert M. Reese

[57] ABSTRACT

Disclosed is a technique for accelerating the Hantzsch reaction, for the clinical determination of triglyceride, so as to permit the reaction to be analytically complete within 15 minutes at 37° C. As is known, in this Hantzsch reaction, one mole of aldehyde is reacted in a solution predominantly containing alcohol and water with two moles of a betadicarbonyl compound in the presence of ammonia to yield, as a colored derivative, a lutidine. In the disclosed technique, the solution also contains an organic accelerator compound. This compound is capable of forming a clear solution with the mixture of components of the reaction solution and is further characterized as having an aprotic internal dipole such that said compound has a distinct center which is electron rich and a center which is electron deficient.

9 Claims, No Drawings

DETERMINATION OF TRIGLYCERIDES

This is a continuation, of application Ser. No. 747,357, filed Dec. 3, 1976, now abandoned.

The present invention relates to the quantitative determination of formaldehyde and, more particularly, to the spectrophotometric or colorimetric determination of formaldehyde as a part of the in vitro clinical diagnostic determination of triglyceride in human serum.

Triglycerides are triesters of glycerol with fatty acids, either saturated such as palmitic acid, or unsaturated, such as oleic acid. The triglycerides are insoluble in water but soluble in several organic solvents. Normally, in human sera, they are complexed with a class of proteins called lipoproteins and in this bound form are transported in the blood stream. The triglycerides enter the body in foods and are also synthesized from many smaller molecules by the body.

Since triglycerides, as well as other lipids, are transported while bound to lipoproteins, the importance for clinical diagnostic purposes of ascertaining the level of triglyceride concentration is closely tied to the liptoprotein diseases (lipoproteinemias). Elevated triglyceride values can be symptomatic of such diseases, which include those such as diabetes mellitus, pancreatitis, glycogen storage disease (von Gierk's disease), and excessive alcohol intake, to name a few.

As described by Biggs, et al., *Clinical Chemistry* 21(3), 437–441 (1975), a typical method for measuring triglycerides involves extraction of the triglycerides from serum, saponification thereof to yield glycerol, oxidation of glycerol to give formaldehyde and the conversion of formaldehyde to a colored or fluorescent material. By measuring color intensity, formaldehyde concentration, and in turn triglyceride concentration, can be quantitatively determined from a calibration graph constructed using calibrators containing known concentrations of triglycerides.

Each of the foregoing steps in the determination of triglycerides is well known. Thus, extraction of triglycerides from serum is generally accomplished with a mixture of an alcohol such as isopropanol, an organic solvent such as heptane and a dilute aqueous acid, such as sulfuric acid. Triglycerides enter the organic layer (generally the upper layer) with the interfering materials remaining in the lower aqueous layer. The combined use of alcohol and acid is necessary during the extraction stage in order to separate the triglycerides from the lipoproteins to which they are bound. To achieve saponification of the triglycerides to yield glycerol, an alkaline base/alcohol mixture such as sodium methoxide, potassium t-butoxide or sodium ethoxide dissolved in isopropanol can be used. Oxidation of glycerol to yield formaldehyde and formic acid is accomplished using the well known Malaprade reaction whereby a sodium periodate solution containing acetic acid and ammonium acetate are added to the glycerol, the yield being 2 moles of formaldehyde and 1 mole of formic acid for each mole of glycerol.

Conversion of formaldehyde to a colored substance is frequently accomplished using the Hantzsch reaction whereby a molecule of an aldehyde, e.g., formaldehyde, is reacted with 2 molecules of a beta-dicarbonyl compound, e.g., acetylacetone (2,4-pentanedione) in the presence of ammonia, such as provided by ammonium acetate, *Heterocyclic Chemistry*, Joule and Smith, p. 75. The lutidine reaction product (from formaldehyde, ammonia, and acetylacetone-3,5-diacetyl-1,4-dihydrolutidine) is a bright yellow compound, the absorbance of which can be determined at 410 nm.

So that the color developing Hantzsch reaction proceeds in a rapid and satisfactory fashion, the reaction mixture is generally heated to above or about 50° C. and ordinarily takes on the order of about 15 minutes for sufficient color development. In contrast, the other reactions involved in the above described triglyceride procedure proceed readily at about room temperature. Accordingly, the fact that the color developing reaction is accomplished at a temperature which is substantially above room temperature is a limiting aspect of the conventional procedures.

Turning now to the present invention, it has been discovered that by including a particular type of accelerator compound in the reaction solution in which the Hantzsch reaction is effected, that reaction can be made to proceed rapidly at a temperature which is substantially below 50° C. Thus, in its broadest aspects, the present invention provides a class of accelerators for the Hantzsch reaction which permits that reaction to be analytically complete within about 15 minutes at 37° C. And, since most clinical laboratories are equipped with 37° C. constant temperature baths, the use of the present invention in the determination of triglycerides as above described is advantageous. As used herein, the term "analytically complete" means that the color developing Hantzsch reaction has proceeded to a point where, after a given time, it is of analytical value, i.e., the color developed is of sufficient intensity and stability so that meaningful quantitative measurements of absorbance can be obtained. To be noted is the fact that, for analytical purposes, complete stoichiometric reaction is not required so long as the measurement of absorbance with respect to the analyte and calibrator is made after the same elapsed reaction time.

In the light of present knowledge, it is difficult, and probably not possible, to discuss the mechanism of the Hantzsch reaction rigorously since it is believed to occur as a series of reactions, with considerable uncertainty as to the exact nature of the intermediate compounds. It is even possible that the final dihydropyridine may form via more than a single series of reactions, Joule and Smith, *Heterocyclic Chemistry*, p. 75; J. A. Berson and E. Brown, *J. Am. Chem. Soc.*, 77, 444, (1955). Further complication is caused by the sensitivity of dihydropyridines to exposure to light, J. A. Berson and E. Brown, *J. Am. Chem. Soc.*, 77, 447 (1955) and the acceleration effects discussed here are reactions taking place in an illuminated environment. The course of the reaction appears to be different when taking place in a cuvet of a spectrophotometer, with illumination by a small light beam at 410 nm, at low intensity. Only the reaction in the presence of light of an intensity commonly utilized in a laboratory is applicable with respect to the noted acceleration. The reactions of dihydropyridines and methods for their syntheses, including the Hantzsch reaction, have been reviewed by U. Eisner and J. Kuthan, *Chem. Rev.*, 72, 1 (1972).

Turning to the accelerator compound utilized in practicing the present invention, it is an organic compound, an important characteristic thereof being that, at about 37° C., it is capable of forming a clear solution with the mixture of components in the clear solution in which the Hantzsch reaction (or series of reactions) is accomplished. Since the invention is directed to determinations utilizing a colorimetric or spectrophotometric detection system, the accelerator compound should not itself be one which might distort the color of the solution which is to be measured. Thus, recognizing that, in the embodiment illustrated herein, the reaction solution contains both organic solvents, e.g., heptane, and alcohol, and water, the accelerator must be what is commonly known as a co-solvent, i.e., a compound which exhibits solubility miscibility with both water and organic liquids.

A further important characteristic of the accelerator compound is that it have an aprotic internal dipole such that the compound has a distinct center which is electron-rich and a center which is electron-deficient. In this respect, it is important to note that both electron-rich and electron-deficient centers in the compound are necessary and that the dipole be aprotic, i.e., not provided by a hydrogen atom. Accordingly, organic compounds containing only protic dipoles or which are simply ionic such as acetic acid or unsubstituted alcohols are not included within those described above.

In general, useful accelerator compounds are nonaromatic compounds which contain strongly electro negative atoms or aromatic compounds containing heterocyclic $\pi$-electron deficient rings. The concept of systems in which carbon atoms of an aromatic ring have either a deficiency or excess of $\pi$-electrons has been described by Adrien Albert in *Heterocyclic Chemistry*, An Introduction, 2nd Ed., Athlone Press (University of London), 1968, pp. 47–68 and references given, pp. 471–512. Compounds containing sulfoxide, sulfone phosphate, halogen or nitrile groups constitute useful types of the former nonaromatic compounds while aromatic compounds containing heterocyclic nitrogen, sulfur, or oxygen atoms typify the latter.

More particularly, the organic accelerator compounds useful herein contain, as the internal dipole providing part, groups which have a positive Hammett substituent constant when substituted in either the meta or para position of benzoic acid. As described by J. Hine in *Physical Organic Chemistry*, 2nd Ed., McGraw-Hill, 1962, pp. 85–88, this constant is a measure of the electron-donating or electron-withdrawing power of a substituent and is defined as log $K'/K_o'$ where $K'$ is the ionization constant (25° C. in water) of benzoic acid containing the substituent and $K_o'$ is the ionization constant (25° C. in water) of benzoic acid. The Hammett substituent constant for a number of groups is given in the above reference as well as by McDaniel and Brown, *J. Org. Chem.* 23, 420 (1958).

Examples of particularly useful accelerator compounds include the following: dialkyl and cyclic sulfoxides such as dimethylsulfoxide, phenylsulfoxide, and thiophan (tetramethylene) sulfoxide; sulfones such as thiophansulfone; alkyl phosphates such as tributyl phosphate; nitriles such as acetonitrile and acetone cyanohydrin,; halogenated alcohols such as hexafluoroisopropanol; pyridine and derivatives thereof such as pyridine-N-oxide 2-acetylpyridine, 2-cyanopyridine, quinaldine, quinoline, isoquinoline, lepidine, 2-picoline, and 2-picoline-N-oxide. Of the enumerated compounds, pyridine-N-oxide appears to be the most rapid accelerator.

The following example illustrates the present invention in connection with the determination of triglyceride in human serum using, as the organic accelerator compound, dimethylsulfoxide. Unless otherwise indicated, all parts and percentages are by weight.

EXAMPLE

Three reagent solutions, denoted respectively as the periodate reagent, methoxide reagent and color reagent, were prepared as follows:

Periodate Reagent

In a 1.00-liter volumetric flask 650 mg of sodium meta-periodate and 77 gm of anhydrous ammonium acetate are placed. About 800 ml of deionized water is added and the mixture stirred until complete solution is attained. Then, 60 ml of concentrated acetic acid is added followed by adding deionized water to give a total volume of 1.00-liter after stirring.

Methoxide Reagent

In a 200 ml volumetric flask 5.0 gm of sodium methoxide solution (25% in methanol, 23 mMol $CH_3O$-$Na$/5gm) are placed and isopropanol added to a total volume of 200 ml. This reagent is stored in a brown glass bottle and should be protected from air and moisture.

Color Reagent 500 ml of color reagent solution is prepared by adding together 30.0 ml of dimethylsulfoxide and 5.0 ml of acetylacetone and diluting the mixture with isopropanol to a total volume of 500 ml.

The Procedure 0.200 ml of serum is placed in a test tube and 1.00 ml of 0.04 M sulfuric acid is added with mixing. Thereafter, 2.00 ml of an isopropanol, heptane solution (55/40 by volume) is added and the solution mixed for 30 seconds and thereafter allowed to stand for about 5 minutes at room temperature to effect phase separation. 0.2 ml of the upper layer (the organic phase) is then transferred to a second test tube and 0.5 ml of the methoxide reagent is then added to the second test tube, and the solution mixed and then allowed to stand for about 10 minutes at room temperature. Then, 1.0 ml of the periodate reagent is added followed by mixing and incubation at room temperature for 5 minutes.

Thereafter, 2.5 ml of color reagent is added, the solution mixed and incubated for 15 minutes at 37° C. and allowed to stand at room temperature for 3 minutes. Absorbance is then read at 410 nm against a reagent blank prepared in similar fashion except that 0.200 ml of water rather than serum is originally employed. In like fashion, a calibrator containing a known concentration of triglyceride is also treated so that the triglyceride level in the serum sample can be quantitatively determined, either from a constructed calibration graph or by calculation. For example, with respect to the latter wherein the calibrator is known to contain 200-mg triglyceride/dl, the calculation is as follows:

$$\text{Triglyceride concentration in serum sample (mg/dl)} = \frac{A_{unknown}}{A_{calibrator}} \times 200 \text{ mg/dl}$$

where A is the measured absorbance for the unknown and the calibrator.

Using the above procedure, Beer's law (linear relationship between concentration and absorbance, intercept equals 0) is followed over the range of 0 to 500 mg/dl. Also, in the foregoing procedure, the Hantzsch color developing reaction is accomplished in an ordinary test tube and, therefore, in the presence of visible light. As mentioned, to effect the noted acceleration, it appears to be important that the reaction be so accomplished which, as a practical matter, is the manner in which the Hantzsch reaction is ordinarily effected in any event.

Thus, as has been illustrated, the present invention provides a manner in which acceleration of the Hantzsch reaction, as explained previously, can be conveniently effected. And, while the invention has been illustrated with respect to the clinical determination of triglyceride, it is considered to be applicable generally to any process wherein a colored derivative of an aldehyde is formed by means of the Hantzsch reaction whereby a molecule of aldehyde is reacted in solution with 2 molecules of a beta-dicarbonyl compound in the presence of ammonia to yield, as the color derivative, a lutidine. In this context, this invention provides an improvement which is realized by having in the reaction solution an organic accelerator compound which is capable of forming a clear solution with the reaction solution and which is characterized as having an aprotic internal dipole such that the compound has a distinct center which is electron rich and a center which is electron deficient.

As to the reaction solution, illustrated herein, the predominant constituents, other than the aldehyde, carbonyl, ammonia and accelerator, are water and alcohol, generally in relative amounts by volume of about 5:1 to 0.5:1 and, preferably, 2:1 to 4:1, of alcohol to water. Organic solvent is present because of the extraction procedure used and, in order to assure miscibility, the volume ratio of organic solvent to water should not exceed about 0.5.

The amount of the accelerator compound utilized in effecting acceleration is not critical so long as it is present in an amount which is effective to permit the reaction to be analytically complete within about 15 minutes at 37° C. As a practical matter, useful amounts of accelerator compound are on the order of about 1 to 25, and preferably 2 to 15 gm. per 500 ml. of color reagent containing acetylacetone in isopropanol. Furthermore, while the invention has been illustrated with respect to conventional procedures for extraction, saponification and oxidation utilizing heptane and isopropanol and specifically identified saponification and oxidation reagents, it is to be understood that it is not to be so limited and, indeed, it is intended to cover all alternative modifications and substituents as can be included within the defined claims. Thus, while heptane has been illustrated as a preferred organic hydrocarbon solvent, other such solvents can be used, the important aspect being that the described extraction procedure can be accomplished. Likewise, alcohols other than isopropanol are suitable.

I claim:

1. In a process for forming a colored derivative of an aldehyde by means of the Hantzsch condensation reaction whereby (one mole) a molecule of aldehyde is reacted in solution with two (moles) molecules of a beta-dicarbonyl compound in the presence of ammonia to yield, as said colored derivative, a lutidine; the improvement wherein, during said reaction, said solution also contains an orgainc accelerator compound dissolved therein which is effective to permit said Hantzsch reaction to be analytically complete within 15 minutes at 37° C., said compound being capable of forming a clear solution with the mixture of components of the reaction solution and being further characterized as having an aprotic internal dipole such that said compound has a distinct center which is electron rich and a center which is electron deficient.

2. The process of claim 1 wherein the organic accelerator compound is a member selected from the group consisting of a dialkysulfoxide, a cyclic sulfoxide, and alkyl phosphate, a nitrile, a halogenated alcohol and a pyridine.

3. The process of claim 2 wherein the accelerator compound is a member selected from the group consisting of dimethylsulfoxide, phenylsulfoxide, thiophan sulfoxide, thiosulfone, tributyl phosphate, acetonitrile, hexafluoroisopropanol, pyridine, 2-acetylpyridine, 2-cyanopyridine and pyridine-N-oxide.

4. The process of claim 3 wherein the accelerator compound is dimethylsulfoxide.

5. The process of claim 1 wherein the aldehyde is formaldehyde, the beta-dicarbonyl compound is acetylacetone, and the lutidine is 3,5-diacetyl-1,4-dihydrolutidine.

6. The process of claim 5 wherein the formaldehyde is formed by oxidation of glycerol which, in turn, has been formed by saponification of triglycerides in a sample of serum.

7. The process of claim 6 wherein the organic accelerator compound is a member selected from the group consisting of a dialkysulfoxide, a cyclic sulfoxide, an alkyl phosphate, a nitrile, a halogenated alcohol and a pyridine.

8. The process of claim 7 wherein the accelerator compound is a member selected from the group consisting of dimethylsulfoxide, phenylsulfoxide, thiophan sulfoxide, thiosulfone, tributyl phosphate, acetonitrile, hexafluoroisopropanol, pyridine, 2-acetylpyridine, 2-cyanopyridine and pyridine-N-oxide.

9. The process of claim 8 wherein the accelerator compound is dimethylsulfoxide.

* * * * *

UNITED STATES PATENT AND TRADEMARK OFFICE
CERTIFICATE OF CORRECTION

PATENT NO. : 4,125,377
DATED : November 14, 1978
INVENTOR(S) : E. Melvin Grindler It is certified that error appears in the above—identified patent and that said Letters Patent is hereby corrected as shown below:

Column 6, lines 28 and 49, "thiosulfone" should read -- thiophansulfone --.

Signed and Sealed this

Twenty-fifth Day of May 1982

[SEAL]

Attest:

Attesting Officer

GERALD J. MOSSINGHOFF
Commissioner of Patents and Trademarks